United States Patent [19]

Huth et al.

[11] Patent Number: 4,778,800

[45] Date of Patent: Oct. 18, 1988

[54] 3-OXADIAZOLE AND 3-CARBOXYLIC ACID BETA-CARBOLINE DERIVATIVES, AND THEIR USE AS PSYCHOTROPIC AGENTS

[75] Inventors: Andreas Huth; Ralph Schmiechen; David N. Stephens, all of Berlin, Fed. Rep. of Germany; Mogens Engelstoft, Vaerlose, Denmark; Frank Waetjen, Bajsvaerd, Denmark; John B. Hansen, Lyngby, Denmark; Leif H. Jensen, Hellerup, Denmark

[73] Assignee: Schering Aktiengesellschaft, Berlin and Bergkamen, Fed. Rep. of Germany

[21] Appl. No.: 929,866

[22] Filed: Nov. 13, 1986

[30] Foreign Application Priority Data

Nov. 13, 1985 [DE] Fed. Rep. of Germany ....... 3540653

[51] Int. Cl.$^4$ .................... A61K 31/40; C07D 471/04
[52] U.S. Cl. ...................................... 514/292; 546/85; 546/87
[58] Field of Search ...................... 546/85, 87; 514/292

[56] References Cited

U.S. PATENT DOCUMENTS

| | | | |
|---|---|---|---|
| 4,435,403 | 3/1984 | Braestrup et al. | 546/86 |
| 4,645,773 | 2/1987 | Englestoft et al. | 546/85 |

FOREIGN PATENT DOCUMENTS

| | | | |
|---|---|---|---|
| 161574 | 5/1984 | European Pat. Off. | 546/85 |
| 110813 | 6/1984 | European Pat. Off. | 546/85 |
| 137390 | 4/1985 | European Pat. Off. | 546/85 |
| 161575 | 11/1985 | European Pat. Off. | 546/85 |
| 3504045 | 2/1985 | Fed. Rep. of Germany | 546/85 |

OTHER PUBLICATIONS

Japanese Patent Abstracts, Appln. Nos. 55-78266 and 55-78031.

*Primary Examiner*—Mary C. Lee
*Assistant Examiner*—J. Richter
*Attorney, Agent, or Firm*—Millen & White

[57] ABSTRACT

Compounds of formula I wherein
X is $COOR^3$ or an oxadiazolyl radical of the formula or
$R^2$ is H, lower alkyl or cycloalkyl,
$R^3$ is lower alkyl,
$R^4$ is hydrogen, lower alkyl or lower alkoxyalkyl,
$R^4$ is $-CHR^1-Z-R^5$,
Z is sulfur or oxygen,
$R^1$ is lower alkyl or optionally substituted phenyl, and
$R^5$ is hydrogen, phenyl or optionally substituted lower alkyl, and wherein each compound can contain 1 or 2 $R^4$ radicals have valuable pharmacological properties.

16 Claims, No Drawings

3-OXADIAZOLE AND 3-CARBOXYLIC ACID BETA-CARBOLINE DERIVATIVES, AND THEIR USE AS PSYCHOTROPIC AGENTS

BACKGROUND OF THE INVENTION

The invention relates to 3-oxadiazole and 3-carboxylic acid ester beta-carboline derivatives, their production and their use as drugs.

SUMMARY OF THE INVENTION

It is an object of this invention to provide new compounds having valuable pharmacological properties.

Upon further study of the specification and appended claims, further objects and advantages of this invention will become apparent to those skilled in the art.

These objects have been achieved by providing the compounds according to the invention of the formula I

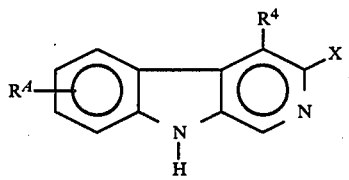

wherein
X is $COOR^3$ or an oxadiazolyl radical of the formula

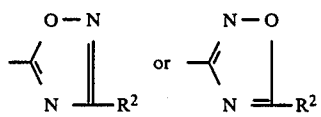

$R^2$ is H, lower alkyl or cycloalkyl,
$R^3$ is lower alkyl,
$R^4$ is hydrogen, lower alkyl or lower alkoxyalkyl,
$R^A$ is $-CHR^1-Z-R^5$,
Z is sulfur or oxygen,
$R^1$ is lower alkyl or optionally substituted phenyl, and
$R^5$ is hydrogen, phenyl or optionally substituted lower alkyl, and wherein each compound can contain 1 or 2 $R^A$ radicals.

The new beta-carboline derivatives of formula I can be substituted once or twice in the A ring in positions 5-8. Substitution in the 5 or 6 position is preferred.

Suitable lower alkyl groups and portions include both straight-chain and branched radicals of $C_1$-$C_6$ carbon atoms, for example, methyl, ethyl, n-propyl, isopropyl, n-butyl, isobutyl, tert-butyl, sec-butyl, a pentyl, a hexyl, etc.

Suitable cycloalkyl radicals $R^2$ can contain 3-7 carbon atoms, radicals with 3-5 carbon atoms being preferred, for example, cyclopropyl, methylcyclopropyl, cyclobutyl, cyclopentyl, etc. Cyclohexyl and cycloheptyl also are included.

The lower alkyl radical $R^5$ can be substituted by one or more halogens, for example, fluorine, chlorine, etc., or $C_{1-2}$ alkoxy groups or phenyl (optionally substituted as described below).

Suitable substituents for phenyl include, for example halogens, such as fluorine, chlorine, bromine, iodine and lower alkyl and alkoxy groups, which can occur 1-3 times in any position of the aromatics.

The compounds according to the invention have valuable pharmacological properties. They influence especially the central nervous system and thus are suitable as psychotropic drugs.

The compounds according to the invention surprisingly show superior psychotropic properties in pharmacological tests in comparison with the beta-carbolines unbranched on the A ring described in European specification No. 54507, as can be seen in Table 1.

TABLE 1

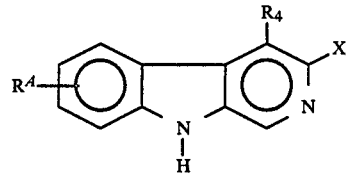

| $R_A$ | $R_4$ | X | $IC_{50}$ ng/ml in vitro | $ED_{50}$ mg/kg in vivo | PTZ $ED_{50}$ (mg/kg) |
|---|---|---|---|---|---|
| 5-$CH_2OC_2H_5$ | $CH_3$ | $COOC_2H_5$ | 0.8 | 1.0 | >100 |
| 5-$CH_2OCH_3$ | $CH_3$ | $COOC_2H_5$ | 0.45 | 2.0 | >100 |
| 5-$CH(CH_3)OC_3H_7$ | $CH_3$ | $COOC_2H_5$ | 0.4 | 0.6 | 1 |
| 5-$CH(CH_3)OC_3H_7$ | $CH_3$ | COO—⟨ | 0.75 | 1.8 | 0.8 |
| 5-$CH(CH_3)OC_2H_5$ | $CH_3$ | (oxadiazolyl-$C_2H_5$) | 0.3 | 0.09 | 0.4 |
| 5-$CH(C_2H_5)OC_2H_5$ | $CH_3$ | (oxadiazolyl-$C_2H_5$) | 0.4 | 3 | 0.6 |

TABLE 1-continued

[Structure: indole-fused ring system with $R_A$ substituent on left benzene ring, $R_4$ substituent at top, X substituent on right, and NH in the five-membered ring]

| $R_A$ | $R_4$ | X | $IC_{50}$ ng/ml in vitro | $ED_{50}$ mg/kg in vivo | PTZ $ED_{50}$ (mg/kg) |
|---|---|---|---|---|---|
| 5-CH(C$_2$H$_5$)OC$_2$H$_5$ | CH$_2$OCH$_3$ | [oxadiazole with C$_2$H$_5$] | 0.2 | 3 | 0.3 |
| 6-CH(CH$_3$)OC$_2$H$_5$ | C$_2$H$_5$ | [oxadiazole with C$_2$H$_5$] | 0.7 | 1.1 | 2.3 |
| 6-CH(CH$_3$)OCH$_2$CF$_3$ | CH$_3$ | COOC$_2$H$_5$ | 0.8 | 1.8 | 2.4 |
| 6-CH(CH$_3$)SC$_2$H$_5$ | CH$_3$ | COOC$_2$H$_5$ | 1.2 | 0.43 | 4 |

It is known that certain sites in the central nervous system of vertebrates exhibit a great specific affinity for the binding of 1,4- and 1,5-benzodiazepines (Squires, R. F. and Braestrup, C., Nature (London) 266 (1977) 734). The binding sites are called benzodiazepine receptors.

The pharmacological properties of the compounds according to the invention were determined by examination of their capability to displace radioactively marked flunitrazepam from benzodiazepine receptors.

The displacement activity of the compounds according to the invention is indicated as $IC_{50}$ and $ED_{50}$ values. The $IC_{50}$ value indicates the concentration which causes a 50% displacement of the specific binding of $H^3$-flunitrazepam (1.0 nM, 0° C.) in samples with a total volume of 0.55 ml of a suspension of brain membranes, e.g., of rats.

The displacement test is performed as follows:

0.5 ml of a suspension of untreated rat forebrain in 25 mM KH$_2$PO$_4$, pH=7.1 (5-10 mg tissue/sample) is incubated for 40-60 minutes at 0° C. together with $^3$H-diazepam (specific activity 14.4 Ci/mmol, 1.9 nM) or $^3$H-flunitrazepam (specific activity 87 Ci/mmol, 1.0 nM). After incubation, the suspension is filtered through a glass filter, the residue is washed twice with cold buffer solution and the radioactivity is measured on the scintillation counter. The test was then repeated but so that before addition of the radioactively marked benzodiazepine a specific amount or an excess amount of the compound, whose displacement activity is to be determined, is added. The $IC_{50}$ value can be calculated on the basis of the values obtained.

The $ED_{50}$ value represents the dose of a test substance, which causes a reduction of the specific binding of the flunitrazepam on the benzodiazepine receptor in a live brain to 50% of the control value.

The in vivo test is performed as follows:

The test substance is injected into groups of mice in different doses and normally intraperitoneally. After 15 minutes the $^3$H-flunitrazepam is administered intravenously to the mice. After another 20 minutes the mice are sacrificed, their forebrain is removed and the radioactivity specifically linked to the brain membranes is measured by scintillation counting. The $ED_{50}$ value is determined from the dose/action curves.

In the pharmacological tests, the compounds according to the invention especially show anxiolytic and anticonvulsive effectiveness. For examination of the anticonvulsive action, stopping of spasms induced by pentylenetetrazole (pentazol) was examined. Pentazol is administered subcutaneously in an amount of 150 mg/kg as a hydrochloric acid solution (pH 2-3) 15-30 minutes after the intraperitoneal application of the test substance. This amount induces clonic and tonic spasms which lead to death in untreated animals. The number of mice which show spasms and the number of them that died 30 minutes after pentazol are recorded.

The $ED_{50}$ values indicated in the table were determined according to the method of Litchfield and Wilcoxon (J. Pharmacol. exp. Ther. 96 (1949) 99-103) as the amount of antagonistically acting substance which protects 50% of the animals from spasms and death.

The new compounds of general formula I thus have valuable pharmacological properties. They particularly affect the central nervous system and thus are suitable as psychotropic drugs to treat mammals, including humans, e.g., for the indications above. The compounds can be used especially for treatment of anxiety accompanied by depressions, epilepsy, sleep disturbances, spasticities, etc., and for muscle relaxation during anesthesia. The compounds according to the invention also show amnestic or memory-promoting properties.

The compounds according to the invention can be used for the formulation of pharmaceutical preparations, for example, for oral and parenteral application in the case of mammals, including man, according to galenic methods known in the art.

Suitable inactive ingredients for formulation of pharmaceutical preparations include those physiologically compatible organic and inorganic vehicles for enteral and parenteral application, which are inert in regard to the compounds according to the invention. As vehicles can be named, for example, water, salt solutions, alcohols, polyethylene glycols, polyhydroxyethoxylated castor oil, gelatins, lactose, amylose, magnesium stearate, talc, silicic acid, fatty acid mono and diglycerides, pentaerythritol fatty acid ester, hydroxymethylcellulose and polyvinylpyrrolidone.

The pharmaceutical preparations can be sterilized and/or mixed with inactive ingredients such as lubricants, preservatives, stabilizers, wetting agents, emulsifiers, buffering agents and dyes.

For parenteral application especially suitable are injection solutions or suspensions, especially aqueous solutions of the active compounds in polyhydroxyethoxylated castor oil.

For oral application especially suitable are tablets, sugar-coated tablets or capsules with talc and/or a hydrocarbon vehicle or binding agent, for example lactose, corn or potato starch. Administration can take place also in liquid form, for example, as a juice to which optionally a sweetening agent is added.

The compounds according to the invention are typically used in a dose unit of 0.05 to 100 mg of active substance in a pysiologically compatible vehicle. The compounds according to the invention are typically administered in a dose of 0.1 to 300 mg/day, preferably 1–30 mg/day, as anxiolytics or anticonvulsants, analogously to the known agent, diazepam.

Production, according to the invention, of the compounds of general formula I takes place according to methods known in the art. For example, the production of the compound of general formula I can occur by
(a) reacting a compound of formula II

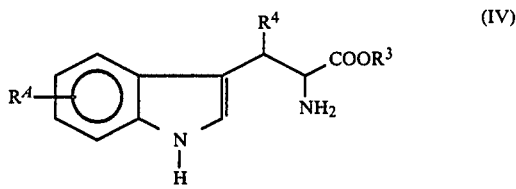

(II)

wherein $R^4$ and $R^{4'}$ have the above-mentioned meanings with a compound of the formula

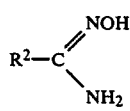

wherein $R^2$ has the above-mentioned meaning, to form a compound of general formula I, in which X is

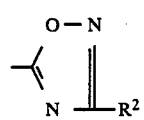

$R^2$ having the above-mentioned meaning,
(b) reacting a compound of formula III

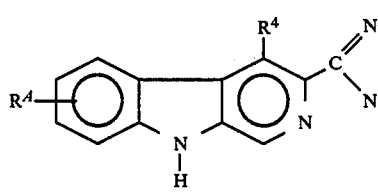

(III)

wherein
$R^4$ and $R^{4'}$ have the above-mentioned meanings, with a carboxylic acid anhydride $(R^2CO)_2O$, wherein $R^2$ has the above-mentioned meanings, to form a compound of the general formula I, in which X

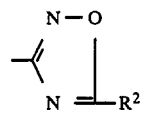

$R^2$ having the above-named meaning,
(c) by cyclizing and aromatizing a compound of formula IV

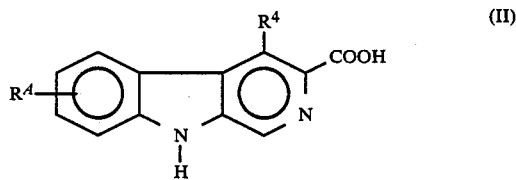

(IV)

wherein
$R^4$ has the above-mentioned meanings,
$R^{4'}$ is hydrogen or is as defined above, and
$R^3$ is methyl or ethyl,
and, if $R^{4'}$ is hydrogen, acylating it to the 6-acyl derivative and reducing the latter to a compound of formula I with $R^{4'}$ meaning $CHR^1OH$, wherein $R^1$ has the above-mentioned meaning, and then optionally etherifying a free hydroxy group and/or transesterifying an ester group.

For the introduction of the 1,2,4-oxadiazol-5-yl radical the beta-carboline carboxylic acid of general formula II is brought to condensation at the reflux temperature of the reaction mixture with an amidoxime of the formula $R^2-C(=NOH)NH_2$, in an inert solvent which boils above 100° C. and is inert in regard to the reactant. Suitable solvents for the condensation reaction include, for example, toluene and dimethylformamide. Appropriately the free beta-carboline-3-carboxylic acid is suitably activated before the condensation reaction. For this purpose, the free acid can be converted, for example, into the mixed anhydride, into the activated ester or into the chloride. Activation to the imidazolide using imidazole/thionyl chloride (or also carbonyliimidazole) in an aprotic solvent such as dioxane, tetrahydrofuran, dimethylformamide or N-methylpyrrolidone at temperatures between 0° and 50° C., preferably room temperature, has also proved successful.

For the introduction of the 1,2,4-oxadiazol-3-yl radical, for example, the 3-carboxylic acid nitrile is reacted with hydroxylamine to form the compound of general formula III. The beta-carboline-3-carboxamidoxime thus obtained is mixed with the acid anhydride $(R^2CO)_2O$ at room temperature and then heated to boiling temperature. The reaction is ended after about 7 hours and working up is done according to the usual process.

Cyclization according to process variant (c) is performed, by dissolving the compound of formula IV in an inert solvent not miscible with water such as benzene, toluene, xylene, chlorobenzene, anisole, mesitylene and reacting it with paraformaldehyde optionally at elevated temperature. The cyclization can also take place with glyoxylic acid. In this case, the amine, which is dissolved in water or in an inorganic solvent, for example, ethyl acetate, is suitably mixed with an aqueous solution of glyoxylic acid at a pH of 0–7, preferably 4. The decarboxylation is performed at elevated temperature, optionally at the boiling temperature of one of the abovementioned inert solvents, for example, toluene or xylene.

Upon cyclization, a 1,2,3,4-tetrahydro-9H-pyrido-[3.4-b]indole derivative is formed which then in both cases is dehydrogenated.

The dehydrogenation can, for example, be performed wherein the initial material is dissolved or suspended in an inert solvent and elementary sulfur is added. The amount of the latter is measured approximately so that per double bond a mole equivalent of sulfur is used. The reaction mixture is refluxed for several hours. The reaction course can be tracked by thin-layer chromatography. All aprotic solvents, whose boiling point is above 100° C. and which are inert in regard to the initial material, for example, xylene, mesitylene, anisole, toluene, chlorobenzene and diphenyl ether are suitable for dehydrogenation.

Another method is dehydrogenation with noble metal catalysts such as platinum in finely divided form, palladium black or palladium carbon in xylene, mesitylene or cumene at 120°–180° C. and reaction times of 2–6 hours.

Another method is dehydrogenation with tert-butyl hypochlorite and tertiary bases (see, e.g., German patent application No. 3 504 045.9).

If a transesterification is desired, it is possible to react, for example, with the corresponding alcohol or alkali alcoholate, optionally titanium tetraisopropylate can be added as catalyst in water-free alcohol. Usually the transesterification is performed at temperatures of 60°–120° C. and is ended after about 2–6 hours.

The introduction of the tert-butyl ester group takes place, for example, by reaction of the carboxylic acid with tert-butoxy-bis-dimethylaminomethane. In general the reaction is performed under an inert gas atmosphere such as argon or nitrogen and with exclusion of moisture at an elevated temperature.

The esters can also be produced by activation of the corresponding acid and subsequent reaction with the desired alcohol.

Aliphatic hydroxy groups are etherified in an inert solvent, for example, methylene chloride, tetrahydrofuran, etc., with an alkyl halide, for example, the chloride, bromide or iodide or an alkyl tosylate in the presence of tetrabutyl ammonium hydrogen sulfate and pulverized KOH. Also a reaction of the hydroxy compound with thionyl chloride at temperatures of −10° C. to +30° C. and subsequent treatment with alcohol is possible.

6-Acyl derivatives can, for example, be obtained under Friedel-Crafts conditions by reaction with acid chlorides in the presence of Lewis catalysts. The acid chlorides preferably are derived from aliphatic $C_{2-4}$ carboxylic acids, for example, acetic acid, propionic acid, butyric acid, etc., and aromatic carboxylic acids, for example, benzoic acid. The ketones thus obtained can, with the usual reduction agents, for example $NaBH_4$, be converted into the corresponding alcohols.

Production of the initial compounds is known or can take place according to known processes from known starting materials.

Thus, the saponification of the ester group can take place in an acidic or alkaline manner; preferably it is saponified in an alkaline manner, by the ester being heated to temperatures up to the reflux temperature of the reaction mixture with dilute aqueous lye such as potassium or sodium hydroxide in a protic solvent, for example, methanol, ethanol or ethylene glycol.

Carboxamidoximes can be produced in known manner from beta-carboline carboxylic acids. The acid amides, as usually represented, can be converted into the corresponding nitriles with water-eliminating agents, for example, a reagent of triphenylphosphine/bromine in the presence of triethylamine. These nitriles can be then reacted with hydroxylamine to the desired carboxamidoximes.

Without further elaboration, it is believed that one skilled in the art can, using the preceding description, utilize the present invention to its fullest extent. The following specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

The necessary carboxylic acids were produced as follows:

500 mg of 5-(1-ethoxyethyl)-4-methyl-beta-carboline-3-carboxylic acid ethyl ester was refluxed with 5 ml of 1N sodium hydroxide solution and 20 ml of ethanol for 3 hours. Then it was acidified with glacial acetic acid, suctioned off and washed with water. 400 mg of 5-(1-ethoxyethyl)-4-methyl-beta-carboline-3-carboxylic acid was obtained, which after good drying over phosphorus pentoxide in a vacuum was further reacted.

Analogously there were produced:
6-(1-hydroxyethyl)-beta-carboline-3-carboxylic acid
6-(1-hydroxyethyl)-4-methyl-beta-carboline-3-carboxylic acid
6-(1-methoxyethyl)-4-methyl-beta-carboline-3-carboxylic acid
6-(1-ethoxyethyl)-4-methyl-beta-carboline-3-carboxylic acid
6-[1-(2,2,2-trifluoroethoxy)-ethyl]-4-methyl-beta-carboline-3-carboxylic acid
6-(1-isopropoxyethyl)-beta-carboline-3-carboxylic acid
6-(1-ethylthioethyl)-4-methyl-beta-carboline-3carboxylic acid
6-(1-ethoxyethyl)-4-ethyl-beta-carboline-3-carboxylic acid
6-(1-butoxyethyl)-beta-carboline-3-carboxylic acid
5-(1-ethoxypropyl)-4-methyl-beta-carboline-3-carboxylic acid
5-(1-ethoxyethyl)-4-methoxymethyl-beta-carboline-3carboxylic acid
6-(1-propoxyethyl)-beta-carboline-3-carboxylic acid
5-(1-methoxyethyl)-4-ethyl-beta-carboline-3-carboxylic acid
6-(1-methoxyethyl)-beta-carboline-3-carboxylic acid
6-(1-hydroxybenzyl)-beta-carboline-3-carboxylic acid
6-(1-hydroxyethyl)-4-ethyl-beta-carboline-3-carboxylic acid
6-(1-phenoxyethyl)-4-methyl-beta-carboline-3-carboxylic acid 5-(1-ethoxypropyl)-4-methoxymethyl-beta-carboline-3-carboxylic acid.

EXAMPLES

EXAMPLE 1

5-(1-ethoxyethyl)-4-methyl-beta-carboline-3-carboxylic acid ethyl ester

A. 25 g (83 mmol) of 1-tosyl-4-hydroxymethyl indole in 600 ml of methylene chloride are mixed by portions with 72.5 g (830 mmol) of manganese(IV) oxide with stirring and cooling. After 4 hours stirring time, the solution is filtered and concentrated.

Yield: 22.8 g of 4-formyl-1-tosyl-indole, mp: 140°–145° C.

B. 22.6 g (86.7 mmol) of chlorotitanium triisopropoxide is suspended in 50 ml of ether under nitrogen at −78° C. with exclusion of moisture. 86.7 mmol of methylmagnesium iodide in 90 ml of ether is added drop by drop. The resulting yellow solution is stirred for 5 minutes at −78° C. and then mixed with 20 g (66.9 mmol) of 4-formyl-1-tosylindole in 150 ml of absolute THF. After 30 minutes at −78° C. it was stirred another 75 minutes at room temperature. Then 25 ml of saturated ammonium fluoride solution and 250 ml of saturated sodium chloride solution were carefully added one after the other. The organic phase was separated and the aqueous phase extracted twice with 200 ml of ethyl acetate. The combined organic phases were dried, filtered and concentrated. The residue was absorptively precipitated with diisopropyl ether.

Yield: 15 g of 4-(hydroxyethyl)-1-tosylindole, mp: 78°–80°

C. 11.9 g (37.8 mmol) of 4-(1-hydroxyethyl)-1-tosyl indole in 150 ml of methylene chloride was mixed at room temperature under argon with 13.3 g (85 mmol) of ethyl iodide, 6.7 g of tetrabutylammonium hydrogen sulfate and 6.7 g (119.3 mmol) of pulverized potassium hydroxide one after the other. The solution was stirred for 2 hours. After filtration over silica gel, the solution was again mixed with equal amounts of ethyl iodide, tetrabutylammonium hydrogen sulfate and potassium hydrogen oxide. The reaction mixture was stirred for 2 hours at room temperature, washed with 200 ml of water and the organic phase dried, filtered and concentrated. Subsequent chromatography on silica gel with cyclohexane/ethyl acetate (8:2) yielded 8.5 g of 4-(1-ethoxyethyl)-1-tosyl indole as oil.

D. 3.75 g (10.9 mmol) of 4-(1-ethoxyethyl)-1-tosyl indole suspended in 15 ml of ethanol was added to a freshly produced solution of 628 mg (27 mmol) of sodium in 25 ml of ethanol and the mixture refluxed 1.5 hours. After evaporation of the solvent the residue was taken up in 50 ml of water and extracted three times with ethyl acetate. The combined organic phases were washed with water, dried, filtered and concentrated.

Yield: 2 g of 4-(1-ethoxyethyl indole); it was used for the subsequent reaction without further purification.

E. A solution of 15 g of acetaldehyde isopropylamine in 5 ml of toluene was added to a solution of 2 g of 4-(1-ethoxyethyl indole) in 10 ml of glacial acetic acid within 30 minutes. After 36 hours at 0°–5° C. the solution was stirred into 50 ml of ice water. The mixture was extracted with toluene and the aqueous phase under ice cooling was adjusted to pH 12 with 2N sodium hydroxide solution. The solution was extracted with ether, washed with half saturated sodium chloride solution and the solvent was evaporated in a vacuum. The raw product (2.8 g) was used for the subsequent reaction without further purification.

F. 2.8 g of amine from reaction E in 150 ml of toluene and 1.3 ml of nitroacetic acid ethyl ester was kept at 80° C. for 4 hours under nitrogen. After cooling, it was washed with 0.1N HCl and water. The solvent was distilled off and the raw product (3.3 g) chromatographed on silica gel with hexane/ethyl acetate.

Yield: 2.7 g of 4-(1-ethoxyethyl)-indole-3-(2-nitro-3-methyl) propionic acid ethyl ester as oil.

G. 2.65 g (7.6 mmol) of 4-(1-ethoxyethyl)-indole-3-(2-nitro-3-methyl) propionic acid ethyl ester was hydrogenated at room temperature and normal pressure for 1.25 hours in 140 ml of ethanol with 4 ml of Raney nickel (type B 115 Z, Degussa Co.). Then the solution was filtered and concentrated.

Yield: 2.3 g of 4-(1-ethoxyethyl)-indole-3-(2-amino-3-methyl) propionic acid ethyl ester as oil.

H. 2.17 g (6.82 mmol) of 4-(1-ethoxyethyl)-indole-3-(2-amino-3-methyl) propionic acid ethyl ester was dissolved in 30 ml xylene and added to 231 mg of suspended paraformaldehyde in 30 ml of xylene. The reaction mixture was refluxed for 75 minutes. Then it was concentrated and chromatographed on silica gel with methylene chloride/ethanol Yield: 1.35 g of 5-(1-ethoxyethyl)-4-methyl-1,2,3,4-tetrahydro-beta-carboline-3-carboxylic acid ethyl ester as oil.

I. 2.25 g (6.8 mmol) of 5-(1-ethoxyethyl)-4-methyl-1,2,3,4-tetrahydro-beta-carboline-3-carboxylic acid ethyl ester in 20 ml of dimethylsulfoxide was stirred with 437 mg of sulfur under argon at 140° C. bath temperature for 30 minutes. After concentration, the oily residue was chromatographed first with hexane/acetone (1:1) and then with methylene chloride/ethanol (10:1).

Yield: 426 mg of 5-(1-ethoxyethyl)-4-methyl-beta-carboline-3-carboxylic acid ethyl ester, mp: 159°–160° C.

Analogously there were produced:

5-(1-methoxyethyl)-4-methyl-beta-carboline-3-carboxylic acid ethyl ester, mp: 161°–163° C.

5-(1-propoxyethyl)-4-methyl-beta-carboline-3-carboxylic acid ethyl ester, mp: 155°–156° C.

5-(1-ethoxypropyl)-4-methyl-beta-carboline-3-carboxylic acid ethyl ester, mp: 185°–186° C.

5-(1-ethoxyethyl)-4-methoxymethyl-beta-carboline-3-carboxylic acid ethyl ester, mp: 144°–148° C.

5-(1-propoxyethyl)-4-methoxymethyl-beta-carboline-3-carboxylic acid ethyl ester 5-(1-methoxyethyl)-4-ethyl-beta-carboline-3-carboxylic acid ethyl ester, mp: 127°–130° C.

EXAMPLE 2

5-(1-ethoxyethyl)-4-methyl-beta-carboline-3-carboxylic acid isopropyl ester 163 mg of 5-(1-ethoxyethyl)-4-methyl-3-carboxylic acid ethyl ester was refluxed for 1 hour in 5 ml of absolute isopropanol with 71 mg of titanium(IV) isopropoxide under argon and exclusion of moisture. After concentration under vacuum, the residue was dispersed in 15 ml of 2N HCl and 15 ml of ethyl acetate. The aqueous phase was shaken out once more with ethyl acetate and alkalized with ammonia whereby titanium oxide precipitated. Also this phase was extracted twice with 15 ml each of ethyl acetate. The organic phases were collectively concentrated and chromatographed over silica gel with acetone/hexane (1:1).

Yield: 66 mg of 5-(1-ethoxyethyl)-4-methyl-beta-carboline-3-carboxylic acid isopropyl ester.

Analogously the following compounds were produced:
5-(1-methoxyethyl)-4-methyl-beta-carboline-3-carboxylic acid isopropyl ester
5-(1-propoxyethyl)-4-methyl-beta-carboline-3-carboxylic acid isopropyl ester, mp: 153°–154° C.
5-(1-propoxyethyl)-4-methoxymethyl-beta-carboline-3-carboxylic acid isopropyl ester
6-(1-propoxyethyl)-4-methyl-beta-carboline-3-carboxylic acid isopropyl ester
6-(1-propoxyethyl)-4-methoxymethyl-beta-carboline-3-carboxylic acid isopropyl ester

EXAMPLE 3

5-(1-ethoxyethyl)-4-methyl-beta-carboline-3-carboxylic acid tert-butyl ester 200 mg of 5-(1-ethoxyethyl)-4-methyl-beta-carboline-3-carboxylic acid was heated in 4 ml of aminal ester for 1.5 hours to 120° C. bath temperature under argon and exclusion of moisture. After concentration, the residue was chromatographed over silica gel with methylene chloride/ethanol (10:1).

Yield: 100 mg of 5-(1-ethoxyethyl)-4-methyl-beta-carboline-3-carboxylic acid tert-butyl ester as oil.

Analogously there was produced:
6-(1-butoxyethyl)-beta-carboline-3-carboxylic acid tert-butyl ester, mp: 189°–191° C.

EXAMPLE 4

6-(1-hydroxyethyl)-beta-carboline-3-carboxylic acid ethyl ester

A. 6-Acetyl-beta-carboline-3-carboxylic acid ethyl ester 400 mg of $AlCl_3$ was suspended in 10 ml of acetyl chloride at 0° C. and 600 mg of beta-carboline-3-carboxylic acid ethyl ester was added. After 5 minutes, 600 mg of $AlCl_3$ was added and the mixture was stirred for 1 hour. Alcohol was added and the pH adjusted to 7–8. 50 ml of water was added and the filtered mixture yielded 450 mg of raw product, which was recrystallized from ethanol/water (1:1). Mp: 290°–305° C.

Analogously there are produced:
6-benzoyl-beta-carboline-3-carboxylic acid ethyl ester
6-acetyl-4-ethyl-beta-carboline-3-carboxylic acid ethyl ester
6-(4-fluorobenzoyl)-beta-carboline-3-carboxylic acid ethyl ester
6-(2-fluorobenzoyl)-beta-carboline-3-carboxylic acid ethyl ester B. 6-(1-Hydroxyethyl)-beta-carboline-3-carboxylic acid ethyl ester 250 mg of the product of A and 150 mg of $NaBH_4$ were stirred in 30 ml of methanol for 2 hours and then refluxed for 30 minutes. Then 30 ml of water was added and the solvent evaporated. 220 mg of oil, which crystallizes overnight, was obtained.
Mp: 125°–130° C.

Analogously the following compounds were produced:
4-methyl-6-(1-hydroxyethyl)-beta-carboline-3-carboxylic acid ethyl ester
6-(1-hydroxybenzyl)-beta-carboline-3-carboxylic acid ethyl ester
6-(1-hydroxyethyl)-4-ethyl-beta-carboline-3-carboxylic acid ethyl ester
6-(1-hydroxy-o-fluorobenzyl)-beta-carboline-3-carboxylic acid ethyl ester, mp: 116°–117° C.
6-(1-hydroxy-p-fluorobenzyl)-beta-carboline-3-carboxylic acid ethyl ester, mp: 212° C.

EXAMPLE 5

4-Methyl-6-(1-methoxyethyl)-beta-carboline-3-carboxylic acid ethyl ester 100 mg of 4-methyl-6-(1-hydroxyethyl)-beta-carboline-3-carboxylic acid ethyl ester was stirred with 10 ml of thionyl chloride at 0° C. for 30 minutes. The product was precipitated by addition of 50 ml of petroleum ether. The precipitated crystals were immediately dissolved in 10 ml of methanol and the solution allowed to stand at room temperature for 2 hours. The product was then precipitated by addition of 20 ml of saturated sodium hydrogen carbonate solution. After suctioning off of the product and washing with water, 50 mg with mp: 96°–97° C. was obtained.

Analogously the following compounds were produced:
4-methyl-6-(1-ethoxyethyl)-beta-carboline-3-carboxylic acid ethyl ester, mp: 90°–91° C.
4-methyl-6-(1-(2,2,2-trifluoroethoxy)-ethyl)-beta-carboline-3-carboxylic acid ethyl ester, mp: 164°–165° C.
4-methyl-6-(1-isopropoxyethyl)-beta-carboline-3-carboxylic acid ethyl ester, mp: 86°–86.5° C.
4-methyl-6-(1-ethylthioethyl)-beta-carboline-3-carboxylic acid ethyl ester, mp: 171°–175° C.
4-ethyl-6-(1-ethoxyethyl)-beta-carboline-3-carboxylic acid ethyl ester
6-(1-butoxyethyl)-beta-carboline-3-carboxylic acid ethyl ester
6-(1-propoxyethyl)-beta-carboline-3-carboxylic acid ethyl ester
6-(1-propoxyethyl)-4-methyl-beta-carboline-3-carboxylic acid ethyl ester
6-(1-propoxyethyl)-4-methoxymethyl-beta-carboline-3-carboxylic acid ethyl ester
6-(1-methoxyethyl)-beta-carboline-3-carboxylic acid ethyl ester, mp: 189°–190° C.
6-(1-phenoxyethyl)-beta-carboline-3-carboxylic acid ethyl ester

EXAMPLE 6

3-[5-(3-Ethyl-1,2,4-oxadiazol)yl]-5-(1-methoxymethyl)-4-methyl-beta-carboline 500 mg of 5-(1-methoxymethyl)-4-methyl-beta-carboline-3-carboxylic acid in 20 mg of absolute dimethylformamide at room temperature was mixed with 500 mg of carbonyldiimidazole and stirred for 4 hours at this temperature. Then 600 mg of propionamioxime was added and stirred overnight at room temperature. After distilling off of the solvent, it was taken up in 50 ml of toluene and cooked on a water separator for 4 hours. After diluting with ethyl acetate, it was, one after the other, shaken out with water and saturated sodium chloride solution dried, filtered and concentrated. The residue was chromatographed over silica gel with hexane/acetone (1:1) as eluant. 250 mg with mp: 213°–214° C. was obtained.

Analogously the following compounds were produced:

3-[5-(3-ethyl-1,2,4-oxadiazol)yl]-6-(1-hydroxyethyl)-beta-carboline, mp: 220°–231° C.
3-[5-(3-ethyl-1,2,4-oxadiazol)yl]-4-methyl-6 (1-hydroxyethyl)-beta-carboline, mp: 263°–267° C.
3-[5-(3-ethyl-1,2,4-oxadiazol)yl]-4-methyl-6-(1-methoxyethyl)-beta-carboline, mp: 255°–265° C.
3-[5-(3-ethyl-1,2,4-oxadiazol)yl]-4-methyl-6-(1-ethoxyethyl)-beta-carboline, mp: 172°–176° C.
3-[5-(3-ethyl-1,2,4-oxadiazol)yl]-4-methyl-6-(1-(2,2,2-trifluoroethoxy)ethyl)-beta-carboline, mp: 140°–155° C.
3-[5-(3-ethyl-1,2,4-oxadiazol)yl]-4-ethyl-6-(1-ethoxyethyl)-beta-carboline, mp: 192°–195° C.
3-[5-(3-ethyl-1,2,4-oxadiazol)yl]-4-methyl-5-(1-ethoxyethyl)-beta-carboline, mp: 180°–184° C.
3-[5-(3-ethyl-1,2,4-oxadiazol)yl]-6-(1-butoxyethyl)-beta-carboline, mp: 220°–226° C.
3-[5-(3-ethyl-1,2,4-oxadiazol)yl]-4-methyl-5-(1-ethoxopropyl)-beta-carboline, mp: 202°–204° C.
3-[5-(3-ethyl-1,2,4-oxadiazol)yl]-4-methoxymethyl-5-(1-ethoxyethyl)-beta-carboline, mp: 175°–178° C.
3-[5-(3-ethyl-1,2,4-oxadiazol)yl]-6-(1-propoxyethyl)-beta-carboline, mp: 225° C.
3-[5-(3-ethyl-1,2,4-oxadiazol)yl]-4-methyl-6-(1-isopropoxyethyl)-beta-carboline, mp: 179°–184° C.
3-[5-(3-ethyl-1,2,4-oxadiazol)yl]-4-methyl-6-(1-ethylthioethyl)-beta-carboline, mp: 165°–170° C.
5-(1-methoxyethyl)-4-ethyl-3-[5-(3-ethyl-1,2,4-oxadiazol)yl]-beta-carboline, mp: 195°–202° C.
6-(1-methoxyethyl)-3-[5-(3-ethyl-1,2,4-oxadiazol)yl]-beta-carboline, mp: 137°–141° C.
6-(1-phenoxyethyl)-4-methyl-3-[5-(3-ethyl-1,2,4-oxadiazol)yl]-beta-carboline, mp: 150°–160° C.
6-(1-hydroxybenzyl)-3-[5-(3-ethyl-1,2,4-oxadiazol)yl]-beta-carboline, mp: 124° C.
6-(1-hydroxyethyl)-4-ethyl-3-[5-(3-ethyl-1,2,4-oxadiazol)yl]-beta-carboline, mp: 174°–177° C.
5-(1-ethoxypropyl)-4-methoxymethyl-3-(3-ethyl-1,2,4-oxadiazol)-5-yl)-beta-carboline The preceding examples can be repeated with similar success by substituting the generic of specifically described reactants and/or operating conditions of this invention and for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of the formula

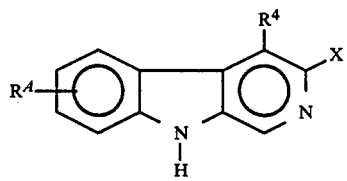

wherein

X is COOR³ or an oxadiazole radical of the formula

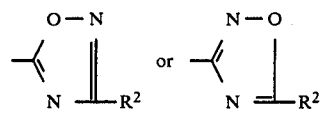

$R^2$ is H, $C_{1-6}$-alkyl or $C_{3-7}$-cycloalkyl,
$R^3$ is $C_{1-6}$-alkyl,
$R^4$ is hydrogen, $C_{1-6}$-alkyl or $C_{1-6}$-alkoxy-$C_{1-6}$-alkyl, n is 1–2,
$R^A$ is —CHR¹—Z—R⁵,
Z is sulfur or oxygen,
$R^1$ is $C_{1-6}$-alkyl, phenyl or phenyl substituted by halogen, $C_{1-6}$-alkyl or $C_{1-6}$-alkoxy, and
$R^5$ is hydrogen, phenyl, $C_{1-6}$-alkyl or $C_{1-6}$-alkyl substituted by halo, $C_{1-2}$-alkoxy, phenyl or phenyl substituted by halogen, $C_{1-6}$-alkyl, or $C_{1-6}$-alkoxy.

2. A compound of claim 1 wherein X is oxadiazole
3. A compound of claim 1 wherein X is COOR³.
4. A compound of claim 1 wherein n is 1.
5. A compound of claim 1 wherein R² is alkyl.
6. A compound of claim 1 wherein $R^A$ is alkyl-O-alkyl.
7. A compound of claim 1 wherein R¹ is alkyl.
8. A compound of claim 1 wherein R⁵ is alkyl
9. A compound of claim 1 wherein $R^A$ is in the 5- or 6-position.
10. A compound of claim 1 wherein $R^A$ is 1-methoxyethyl, 1-ethoxyethyl, 1-propoxyethyl, 1-ethoxypropyl, 1-butoxyethyl, 1-hydroxyethyl, 1-ethylthioethyl, or 1-(2,2,2-trifluoroethoxy)ethyl.
11. 5-(1-ethoxyethyl)-4-methyl-beta-carboline-3-carboxylic acid ethyl ester 5-(1-methoxyethyl)-4-methyl-beta-carboline-3-carboxylic acid ethyl ester 5-(1-propoxyethyl)-4-methyl-beta-carboline-3-carboxylic acid ethyl ester 5-(1-ethoxyethyl)-4-methoxymethyl-beta-carboline-3-carboxylic acid ethyl ester 5-(1-propoxyethyl)-4-methyl-beta-carboline-3-carboxylic acid isopropyl ester 6-(1-ethoxyethyl)-4-methyl-3-(ethyl-1,2,4-oxadiazol-5-yl)-beta-carboline 6-(1-ethoxyethyl)-4-ethyl-3-(3-ethyl-1,2,4-oxadiazol-5-yl)-beta-carboline 5-(1-ethoxypropyl)-4-methoxymethyl-3-(3-ethyl-1,2,4-oxadiazol-5-yl)-beta-carboline 5-(1-ethoxypropyl)-4-methyl-3-(3-ethyl-1,2,4-oxadiazol-5-yl)-beta-carboline 5-(1-ethoxyethyl)-4-methyl-3-(3-ethyl-1,2,4-oxadiazol-5-yl)-beta-carboline 5-(1-ethoxyethyl)-4-methyl-beta-carboline-3-carboxylic acid-tert-butyl ester 5-(1-butoxyethyl)-beta-carboline-3-carboxylic acid-tert-butyl ester 6-(1-hydroxyethyl)-beta-carboline-3-carboxylic acid ethyl ester 4-methyl-6-(1-methoxyethyl)-beta-carboline-3-carboxylic acid ethyl ester 4-methyl-6-(1-ethoxyethyl)-beta-carboline-3-carboxylic acid ethyl ester 4-methyl-6-(1-(2,2,2-trifluoroethoxy)-ethyl)-beta-carboline-3-carboxylic acid ethyl ester or 4-methyl-6-(1-ethylthioethyl)-beta-carboline-3-carboxylic acid ethyl ester, each a compound of claim 1.
12. A pharmaceutical composition for inducing a psychotropic effect in a subject comprising a compound of claim 1 and a pharmaceutically acceptable carrier.
13. A pharmaceutical composition for inducing a pyschotropic effect in a subject comprising 0.05 to 100 mg. of a compound of claim 1 and a pharmaceutically acceptable carrier.
14. A method of achieving an anxiolytic effect comprising administering to a patient an effective amount of a compound of claim 1.
15. A method of achieving an anticonvulsant effect comprising administering to a patient an effective amount of a compound of claim 1.
16. A method of binding a benzodiazepine receptor comprising administering to a patient an effective amount of a compound of claim 1.

* * * * *